United States Patent [19]

Epstein

[11] Patent Number: 5,306,731
[45] Date of Patent: Apr. 26, 1994

[54] METHOD AND PRODUCTS FOR TREATING THE EYE

[75] Inventor: David L. Epstein, Wayland, Mass.

[73] Assignee: Massachusetts Eye and Ear Infirmary, Boston, Mass.

[21] Appl. No.: 669,381

[22] Filed: Mar. 14, 1991

Related U.S. Application Data

[63] Continuation-in-part of Ser. No. 514,488, Apr. 26, 1990, which is a continuation-in-part of Ser. No. 123,797, Nov. 23, 1987, which is a continuation-in-part of Ser. No. 745,325, Jun. 14, 1985, abandoned.

[51] Int. Cl.$^5$ .................... A61K 31/195; A61K 31/19
[52] U.S. Cl. .................................. 514/562; 514/571; 514/913
[58] Field of Search ........................ 514/571, 562, 913

[56] References Cited

U.S. PATENT DOCUMENTS

| | | | |
|---|---|---|---|
| 4,590,210 | 5/1986 | Landham | 514/548 |
| 4,596,771 | 6/1986 | Cidlowski et al. | 435/7 |
| 4,777,130 | 10/1988 | Maes | 435/7 |
| 4,826,879 | 5/1989 | Yamamoto et al. | 514/657 |
| 4,829,011 | 5/1989 | Gibbons | 436/512 |
| 4,847,209 | 7/1989 | Lewis et al. | 436/533 |
| 4,891,324 | 1/1990 | Pease et al. | 436/519 |
| 4,965,192 | 10/1990 | Maes | 435/7 |

FOREIGN PATENT DOCUMENTS

| | | |
|---|---|---|
| 883792 | 10/1971 | Canada. |
| WO86/07259 | 12/1986 | PCT Int'l Appl.. |
| 1141422 | 1/1969 | United Kingdom. |

OTHER PUBLICATIONS

Epstein et al., "Influences of glutathione and sulfhydryl containing compounds on aqueous humor outflow function," Chem. Abst. vol. 113:523 (Aug. 27, 1990).
Epstein et al., "N-ethylmaleimide increases the facility of aqueous outflow of excised monkey & calf eyes", Invest. Ophthalmol. Vis. Sci. 22:752-756 (1982).
Magro et al., "Effect of sulfhydryl-reactive ATPase inhibitors upon mast cell and basophil activation", Int. Archives of Allergy and Applied Immunology 77:41-45 (1983).
Epstein et al., "The effect of diamide on lens glutathione and lens membrane function", Invest. Ophthalmol. Vis. Sci. 9:629-638 (1970).
Lindenmayer et al., "Morphology and Function of the Aqueous Outflow System in Monkey Eyes Perfused with Sulfhydryl Reagents", Invest. Opthalmol. Vis. Sci. 24:710-717 (1983).
Epstein et al., "Effect of iodacetamide perfusion on outflow facility and metabolism of the trabecular meshwork", Invest. Ophthalmol. Vis. Sci. 20:625-631 (May 1981).
Anderson et al., "Metabolism of calf trabecular (reticular) meshwork", Invest. Ophthalmol. Vis. Sci. 19:13-20 (Jan. 1980).
Kahn et al., "Glutathione in Calf Trabecular Meshwork and its Relation to Aqueous Humor Outflow Facility", Invest. Ophthalmol. Vis. Sci. 24:1283-1287 (1983).
Scott et al., "Glutathione Peroxidase of Calf Trabecular Meshwork", Invest. Ophthalmol. Vis. Sci. 25:599-602 (1984).
Freddo et al., "Influence of Mercurial Sulfhydryl Agents on Aqueous Outflow Pathways in Enucleated Eyes", Invest. Ophthalmol. Vis. Sci. 25:278-285 (1984).
Epstein et al., "The Biochemistry of Outflow Mechanisms", Applied Pharmacology in the Medical Treatment of Glaucomas pp. 135-150 (Aug. 1984).

(List continued on next page.)

Primary Examiner—Zohreh Fay
Attorney, Agent, or Firm—Wolf, Greenfield & Sacks

[57] ABSTRACT

This invention is directed to improved treatment for glaucoma. It involves delivering to the eye molecules which increase the outflow of aqueous humor, in conjunction with masking agents. The masking agents reduce the side effects of the therapeutically active molecules by masking the sulfhydryl reactive groups on the molecules. The masking agents can be delivered separately from the molecules, or as adducts of the molecules.

27 Claims, No Drawings

OTHER PUBLICATIONS

Epstein, D. L., "Open Angle Glaucoma", Arch. Ophthalmol. 105:1187–1188 (Sep. 1987).

Epstein et al., "Influence of Etharcynic Acid on Outflow Facility in the Monkey and Calf Eye", Invest. Ophthalmol. Vis. Sci. 28:2067–2075 (1987).

Epstein et al., "Paracellular Outflow Routes Through the Inner Wall of Schlemm's Canal in Cynomolgus Monkeys", Arvo Abstract (1988).

Ozment et al., "The Effect of Intracameral Ethacrynic Acid on Intraocular Pressure of Living Monkeys", Arvo Abstract (1988).

Peczon et al., "Diuretic Drugs in Glaucoma", American Journal of Opthalmology 66:680–683 (Oct. 1968).

Guenther et al., "Superficity of ethacrynic acid as a sulfydryl reagent", Pharmacodynamics 84:99192h p. 23 (1976).

Koechel et al., "Diuretic activity of Mannich base derivatives of ethacrynic acid and certain ethacrynic acid analogs", Chemical Abstracts 89:53289 (1978).

Cragoe et al, "(1-Oxo-2-halo-5-indanyloxy)alkanoic acids", Chemical Abstracts 82:17084 (1975).

Cragoe et al., "Diuretic and saluretic (1-oxo-2-alkylidene-5-indanyloxy(thio)acetic acids", Chemical Abstracts 73:25182f (1970).

Cragoe and Woltersdorf, "Diuretic and saluretic substituted (1-oxoinden-5-yl-oxy)acetic acids", Chemical Abstracts 73:25181e (1970).

Cragoe et al., "Antiinflammatory 3,4-dihydro2H pyran", Heterocyclic Compounds 71:91305h (1969).

Cragoe et al., "a[(a-Methylenealkanoyl)phenoxy]alkanoic acids", Chemical Abstracts 71:70324y (1969).

Merck & Co., Inc., "2-(Hydrocarbyipolythiomethyl)alkanoyl phenoxyacetic acids", Chemical Abstracts 66:104824a (1967).

Epstein et al., "Ethacrynic Acid Uniquely Disrupts Cellular Tubulin in Trabecular and Other Endothelial Cells", Arvo Abstract (1991).

Hooshmand and Epstein, "Thiol Adducts of Ethacrynic Acid Increase Outflow Facility in Enucleated Calf Eyes", Arvo Abstract (1991).

Schroeder et al., "Topical Ethacrynic Acid Lowers Intraocular Pressure in Rabbits and Monkeys", Arvo Abstract (1991).

Gere, M., "Risk of postcataract IOP spike justified prophylactic drugs", Ocular Surgery News vol. 8, No. 14 (1990).

Koechel and Cafruny, "Thiol Adducts of Ethacrynic Acid: A Correlation of the Rate of Liberation of Ethacrynic Acid w/the Onset & Magnitude of the Diuretic Response", The Journal of Pharmacology and Experimental Therapeutics 192:179–194 (1975).

Cragoe, E. J., "The (Aryloxy)acetic Acid Family of Diuretics", J. Clin. Pharmacol. 9, 577:203–223 (1980).

Liang et al., "Ethacrynic Acid Increases Facility of Outflow in the Human Eye In Vitro", Arvo Abstracts 1849 (1990).

Green and Mayberry, "Drug Effects on the Hydraulic Conductivity of the Isolated Rabbit Ciliary Epithelium", Quarterly J. Exp. Physiol. 70:271–281 (1985).

Neubauer and Severin, "Glaukom", Therapiewocke 25:7467–7470 (1975).

Epstein et al., "The Search for a Sulfhydryl Drug for Glaucoma", Invest. Opthalmol. Vis. Sci. 27 (Suppl. 3) 179 (1986).

METHOD AND PRODUCTS FOR TREATING THE EYE

CROSS REFERENCE TO RELATED APPLICATIONS

This is a continuation-in-part of application Ser. No. 514,488 filed Apr. 26, 1990, which is a continuation-in-part of application Ser. No. 123,797 filed Nov. 23, 1987, which is a continuation-in-part of application Ser. No. 745,325 filed Jun. 14, 1985 abandoned. The specifications and disclosures of all of the foregoing applications are incorporated herein by reference.

BACKGROUND OF THE INVENTION

Glaucoma is any condition of the eye characterized by elevated intraocular pressure. It may be chronic or acute, and may be due to disease, injury, or the result of conventional operative techniques. Glaucoma can cause loss of sight, loss of light perception and/or intense pain.

There are various treatments for glaucoma, although none are entirely satisfactory for all indications. A relatively recent advance in the treatment of glaucoma is disclosed in U.S. Pat. No. 4,757,089 to Dr. David L. Epstein. This patent discloses a method for treating glaucoma by increasing aqueous humor outflow in the eye of a patient, thereby reducing intraocular pressure. Increasing outflow is accomplished by treating the eye with a molecule that contains a group capable of reacting with the sulfhydryl groups in the trabecular meshwork of the eye, and in particular treating the eye with ethacrynic acid and analogs thereof.

The present invention involves substantial improvements to the subject matter of the foregoing patent.

SUMMARY OF THE INVENTION

The invention involves the safe and effective treatment of the eye with molecules that contain one or more groups capable of reacting with sulfhydryl groups in the trabecular meshwork of the eye. In conjunction with delivering the sulfhydryl-reactive molecule to the eye, a masking agent is administered in sufficient amount to prevent medically unacceptable side effects, which otherwise could occur without administering the masking agent. The masking agent forms with the sulfhydryl-reactive molecule an adduct, thereby protecting the sulfhydryl groups of the cornea from harmful chemical interaction with the molecule. The methods and products of the invention are particularly useful in treating or preventing glaucoma.

One aspect of the invention features topical application of the foregoing adduct, and preferred adducts are those of ethacrynic acid or analogs thereof. Application of an excess of masking agent can improve the results. The topical treatment may include administration of a delivery enhancing agent as well. The adducts, masking agents and delivery enhancing agents may be provided in pharmaceutically acceptable ophthalmic preparations and may be contained in containers constructed and arranged to deliver topically to the eye the ophthalmic preparations.

The invention provides effective, non-surgical treatment of glaucoma in a manner to increase fluid outflow while preventing medically unacceptable side effects. Other features and advantages of the invention will be apparent from the following description of the preferred embodiments thereof, and from the claims.

DETAILED DESCRIPTION OF THE PREFERRED EMBODIMENTS

As described above, the invention involves the treatment of glaucoma with sulfhydryl-reactive molecules used in conjunction with masking agents. It has been discovered that when therapeutically active molecules bearing sulfhydryl reactive groups are applied to the eye, medically unacceptable side effects may follow. One such side effect is corneal edema. Corneal edema is a condition evidenced by abnormal accumulation of fluid within the intercellular spaces of the cornea. Clinical symptoms of corneal edema include corneal haziness and increased corneal thickness, apparent upon ophthalmoscopic examination. A major cause of corneal edema is impaired function of the corneal endothelium, the cell layer covering the inner surface of the cornea, in response to certain chemicals or conditions. The corneal endothelium is known to possess sulfhydryl groups.

According to one aspect of the invention, medically unacceptable side effects, in particular corneal edema, can be avoided by creating conditions which reduce or prevent the interaction between the sulfhydryl reactive groups of the therapeutic molecules and the sulfhydryl groups in the corneal cells. This may be accomplished by delivering the molecules in conjunction with masking agents. These masking agents are biocompatible, and bind reversibly to the sulfhydryl reactive groups on the therapeutically active molecules. The compound formed by the binding of the therapeutically active molecule and the masking agent is called an adduct. When topically applied to the surface of the eye, such an adduct crosses the cornea without causing corneal edema. Surprisingly, the topical application of the adduct still results in an increase in aqueous humor outflow. Thus, the use of the masking agent, by decreasing medically undesirable side effects and increasing the margin of safety, allows the use of therapeutic compounds at dosages which would otherwise be clinically unacceptable.

Although not wishing to be bound by any theory of the invention, it is believed that the adducts pass through the cornea and then enter the aqueous humor where they dissociate to release the therapeutically active molecules. The sulfhydryl reactive groups on these molecules then may react with the sulfhydryl groups in the trabecular meshwork, as described in U.S. Pat. No. 4,757,089 (Epstein, issued Jul. 12, 1988, the entire disclosure of which is incorporated herein by reference), causing an increase in the outflow of aqueous humor from the eye, which is beneficial in the medical management of glaucoma.

The preferred molecules useful in the methods of the invention have a number of properties, now discussed in greater detail.

Sulfhydryl Reactivity

The molecules contain chemical groups which are capable of reacting with the sulfhydryl groups of the trabecular meshwork to increase aqueous humor outflow. The molecules react with the sulfhydryl groups in a manner which does not cause an unacceptable amount of swelling of the cells of the trabecular meshwork, particularly the inner wall endothelial cells of Schlemm's canal, because swelling can decrease outflow. "Unacceptable amount of swelling", as used herein, means an amount of swelling which counteracts the outflow increasing effects of the compounds, resulting in no net outflow increase. Whether swelling is caused by a particular compound can be determined by testing the compound in the system described in Epstein et al. (1982) Invest. Ophthalmal. Vis. Sci. 22, 6, 752-756, and examining the trabecular meshwork cells morphologically.

Suitable sulfhydryl reactive groups include C=C, C=O, sulfhydryl, alkyl (e.g., methyl or ethyl) and aryl (e.g., phenyl) substituted with a good leaving group, e.g., halogen, tosyl, or mesyl. Preferably, in the case of substituted alkyl groups, substitution is primary, rather than secondary or tertiary, for greater reactivity.

In the preferred embodiment, the therapeutically active molecule is ethacrynic acid. The structural formula of ethacrynic acid is:

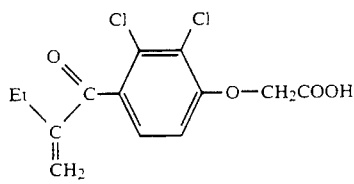

Other embodiments of suitable therapeutically active molecules include analogs of ethacrynic acid. An analog is a molecule which is structurally similar to the parent molecule, and is capable of achieving the same or substantially the same function or activity in terms of increasing aqueous humor outflow. Specific embodiments of suitable molecules of the invention include analogs of ethacrynic acid and their ester or amide derivatives, and pharmaceutically acceptable salts thereof, being of the general formula

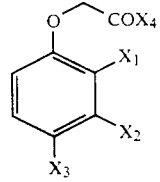

wherein each $X_1$ and $X_2$, independently, is a halogen, H, or $CH_3$, or $X_1$ and $X_2$ together form a substituted or unsubstituted aromatic ring; $X_3$ is a organic group, preferably, a sulfhydryl reactive organic group as defined above; $X_4$ is OH or an organic group; and where, preferably, each $X_1$ and $X_2$, independently, is H, Cl, $CH_3$, or $X_1$ and $X_2$ together form a phenyl ring; $X_3$ is one of chloropropanoyl, tosyl or mesyl; and $X_4$ is one of hydroxy, amino or alkoxy. Specifically, preferred embodiments of analogs of ethacrynic acid include the following molecules:

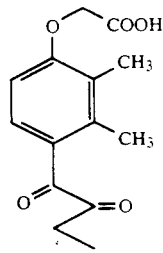

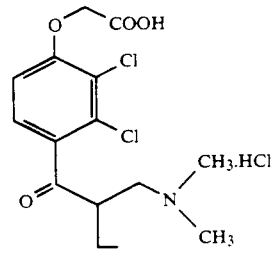

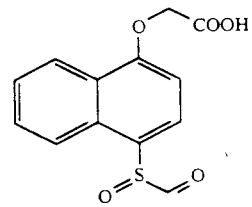

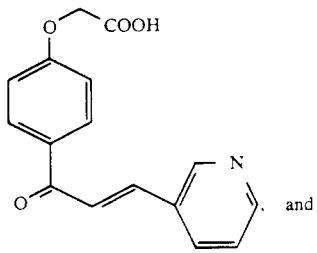

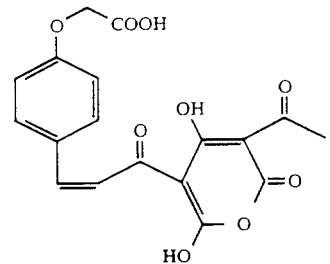

Medically unacceptable side effects, which may result from interaction of the molecules described above with corneal sulfhydryl groups, are prevented by masking the sulfhydryl reactive groups of the therapeutically active molecules with a masking agent in a reversible chemical reaction. A masking agent is an agent which is capable of preventing the sulfhydryl reactive group of the therapeutically active molecule from participating in chemical reactions with the sulfhydryl groups on and within the cornea. The kinetics of the binding reaction between the active molecule and masking agent are such that while corneal toxicity is prevented by formation of the adduct, the adduct dissociates, allowing outflow-increasing interaction between the unbound active molecule and the sulfhydryl groups of the trabecular meshwork.

The masking agent reacts with the sulfhydryl reactive group of the active molecule by the conjugate addition reaction known as the Michael reaction. An example of chemical systems that undergo the Michael reaction is alpha, beta-unsaturated carbonyl compounds of general formula I. Nucleophiles (:Nu) readily add to I to yield the Michael addition produce II. One chemical property of the Michael reaction is its reversability under which the addition product may disassociate to yield the two reactants. In the presence of another nucleophile (:B) an exchange reaction may occur to yield a different Michael addition product (III). This subsequent Michael reaction may proceed either in a stepwise manner (path a) or by way of a concerted mechanism (path b).

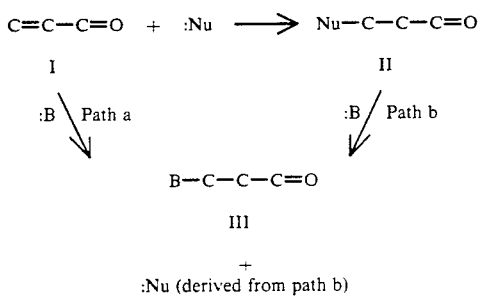

:Nu (derived from path b)

To illustrate the Michael reaction more specifically, a reaction is shown below, with ethacrynic acid (IV) depicted as the therapeutically active molecule, and RSH as the masking agent. The compound V is an adduct of ethacrynic acid. The reaction is reversible, with the dissociation of the adduct occurring by a retro Michael reaction.

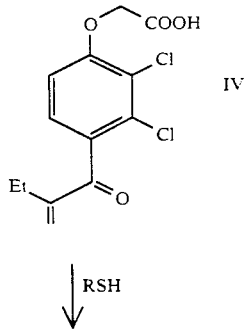

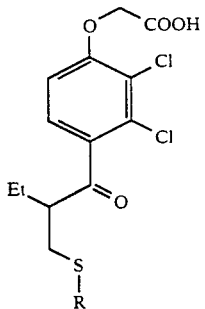

The masking agent is administered in conjunction with the therapeutically active molecule. By "in conjunction with" it is meant that the masking agent is administered coupled to the therapeutically active molecule as an adduct, uncoupled but substantially simultaneously with the active molecule, or in addition to a formed adduct. By substantially simultaneously, it is meant that the molecule and the masking agent are administered close enough in time to beneficially protect sulfhydryl groups within the cornea from reacting with the sulfhydryl reactive groups of the active molecule. The masking agent may be administered in equimolar amount with the active molecule or adduct, or may be administered either in molar excess or deficit to the therapeutically active molecule. The ideal relative amounts will depend upon the particular active molecule and masking agent selected, the kinetics of their binding, the manner of their administration and the particular condition they are being administered to treat. These factors are of the type which those of ordinary skill in the art are capable of evaluating.

The masking agent must be biocompatible, meaning that it causes no medically unacceptable side effects when administered to the eye either separately or as a component of an adduct or therapeutic mixture. The masking agent may be any compound which is biocompatible, undergoes a Michael reaction with the sulfhydryl reactive group of the therapeutically active molecules characterized above, and which has acceptable reaction kinetics for the therapeutic efficacy in treatment of glaucoma while preventing corneal edema. While many others will be apparent to those skilled in the art, the following are examples of masking agents:

TABLE I

| | |
|---|---|
| SH—CH₂—CH—(NH₂)—COOH | cysteine |
| SH—CH₂—CH₂—NH₂·HCl | mercaptoethylamine |
| 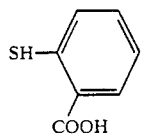 | thiosalicylic acid |
| SH—CH₂—CH₂—COOH | 3-mescaptopropionic acid |
| 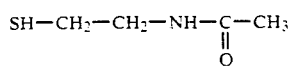 | N-acetyl mercaptoethylamine |

TABLE I-continued

| Structure | Name |
|---|---|
| SH—⬡ | thiophenol |
| SH—⬡(2,5-Cl)—OH | 4-mercaptophenol |
| SH—⬡ | 2,5-dichlorobenzenethiol |
| SH—⬡(3,4-Cl) | 3,4-dichlorobenzenethiol |
| SH—CH₃ | methanethiol |
| SH—O—CH₃ | methansulfinic acid |
| SH—C—(CH₃)₃ | tertiary butylthiol |
| SH—(CH₂)₃—Cl | 3-chloropropanethiol |
| SH—CH₂—CH=CH₂ | allylthiol |
| SH—CH₂—⬡ | benzylthiol |
| SH—CH₂—CH—S—CH₂—OH | 1-hydroxymethylethanedithiol |
| SH—CH₂—COOH | mercaptoacetic acid |
| SH—CH₂—CH—(NH—CO—CH₃)—COOH | N-acetylcysteine |
| SH—CH₂—CH₂—CH—(NH₂)—COOH | |
| (+H₃—N—CH(COOH)—CH₂—CH₂—CO—NH—CH(CH₂SH)—CONHCH₂—COOH) | glutathione |
| SH—CO—CH₃ | thioacetic acid |
| SH—O—CH₂—C₆—H₅ | |
| SH₂ | dihydrogen sulfide |
| NH—(CH₃)₂ | dimethylamine |
| pyridine ring | pyridine |
| pyrazole ring | pyrazole |
| imidazole ring | imidazole |

TABLE I-continued

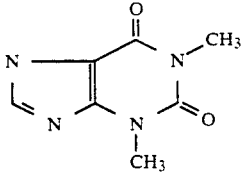

theophylline

The preferred masking agents are cysteine, cysteamine, N-acetylcysteine, N-acetylcysteamine, glutathione, or thiosalicylic acid. The most preferred is cysteine as the adduct-forming masking agent and N-acetylcysteine applied separately in molar excess.

The invention is useful whenever medically unacceptable side effects may occur as a result of delivering a therapeutically effective amount of a compound with sulfhydryl reactive groups to the trabecular network. This includes treatment of existing chronic and acute conditions, as well as prophylactic treatment to prevent such conditions. The adducts or masking agents of the invention may be administered topically to the eye, by intracameral injection, when reforming the anterior chamber after surgery, or systemically. The preferred manner of administration is topical.

When administered topically, the compounds of the invention are delivered in a medically acceptable ophthalmic preparation. Such preparations may routinely contain pharmaceutically acceptable concentrations of salts, buffering agents, preservatives, thickening agents, chelating agents, wetting agents, and delivery enhancing agents. A delivery enhancing agent is a substance that facilitates the delivery of the therapeutic compound of the invention into the aqueous humor, including substances which increase corneal permeability, such as surfactants, wetting agents, liposomes, DMSO, and agents which mildly disrupt the corneal surface. A wetting agent is a substance which evenly coats the outer corneal surface. A preferred wetting agent is benzalkonium chloride. Other examples of wetting agents include sorbitan esters and polyoxyethylene ethers.

The adducts and masking agents of the invention are administered in therapeutically effective amounts. A therapeutically effective amount is one which causes a medically useful increase in outflow of aqueous humor from the eye.

The adducts and masking agents of the invention are administered in nontoxic amounts with acceptable margins of safety. As used herein, "margin of safety" refers to the ratio of the dosage of the outflow increasing molecules which causes medically unacceptable side effects, and the dosage which causes substantial (i.e., medically useful) increase in aqueous humor outflow in treating or preventing glaucoma (e.g., in a typical patient with open angle glaucoma). The margin of safety of the molecules must be at least 2.0, and more preferably at least 4.0. It is also important that the molecules not produce, at effective dosages, long-term deleterious changes in the eye.

The compounds of the invention are for treatment of glaucomatous conditions in eyes of mammalian subjects (e.g., humans, dogs and cats).

The adducts and masking agents of the invention may be supplied in different containers and forms. In one embodiment, the adducts and/or masking agent will be supplied in the form of a solution in a bottle constructed and arranged to facilitate administration of the solution as eyedrops. Such a bottle may have a dropper tip as the upper part, with a detachable cap which seals the dropper tip when the cap is replaced on the bottle. An alternative bottle may have a separable dropper instrument which is attached to the bottle cap, and which is contained inside the bottle when the cap is replaced.

The adducts and molar excess of masking agent, if present, may be supplied in a single container or in separate containers. In one embodiment, the therapeutically active molecules and masking agent are supplied in separate containers, adducts being formed only after administration.

In another embodiment, the adducts and/or masking agents of the invention are supplied as a lyophilized powder within the lower chamber of a two chamber vial. The upper chamber contains sterile diluent or sterile and pyrogen-free diluent. Access to the chambers is provided by frangible membranes. In use, the membranes are pierced by the needle of a syringe, and the diluent flows into the lower chamber, dissolving the lyophilized powder. In another embodiment, the upper and lower chambers are constructed and arranged within a syringe, wherein the action of advancing the plunger of the syringe causes the contents of the two chambers to mix. In these embodiments, the diluent may contain sterile water, organic and inorganic electrolytes, and buffering agents. Examples of inorganic electrolytes include, but are not limited to, the chlorides of sodium, potassium, calcium and magnesium. Suitable buffering agents may include the sodium or potassium salts of boric acid, citric acid, phosphoric acid, acetic acid and the like. The lyophilized powder of the invention may contain, in addition to the active ingredient, other pharmaceutically acceptable inert ingredients such as bulking agents, electrolytes, and buffering agents.

Suitable bulking agents include mannitol and dextran. Acceptable electrolytes include the chlorides of sodium, potassium, magnesium and calcium. Buffering agents may be taken from the group of mono- or disodium or potassium salts of boric acid, citric acid, phosphoric acid, or acetic acid.

Thus, the components in the lyophilized powder and the vehicle for reconstitution may be adjusted such that the final formulation for injection is compatible with osmolarity and pH of the aqueous humor. Acceptable osmolarity may be in the range of 150 to 350 mOsm/kg, while pH of the formulation may vary from 6.2-7.8.

The compounds of the invention and appropriate solutions for their use may be supplied in suitable containers in the form of kits. These kits may include instructions for use, useful additional implements, and may be supplied in a sterile condition in impervious protective covering.

EXAMPLES

In Vitro Use of An Adduct of the Invention

Enucleated calf eyes were obtained from a local abattoir and were transferred on cold normal saline. Upon receipt, the eyes were placed in a beaker filled with normal saline into a water bath set at 25° C. Calf eye corneas were trephined and Grant corneal fittings were attached to allow fluid flow to enter the eye. Because the eye is a closed system, the facility of outflow was measured in microliters of fluid to enter the eye per mm Hg per minute. Two pairs of calf eyes were perfused during each experiment with a mock aqueous fluid: Dulbecco's phosphate buffered saline containing calcium chloride and 5.5 mM glucose.

The calf eyes were perfused at 15 mm Hg for 1 hour and then a baseline facility measurement was obtained. The anterior chamber fluid was then exchanged with a drug solution for the experimental eye and sham for the control eye. The calf eyes were perfused with the drug or sham solution from an attached reservoir for an additional five hours, during which facility measurements were taken hourly. Drug effects can be found by comparing the amount of fluid which entered the experimental calf eyes compared to that of the control eyes from the baseline measurement to the end of the experiment.

The following summary chart contains results from many experiments.

In Vivo Use of An Adduct of the Invention

A mixture of ethacrynic acid (sodium salt) and L-cysteine applied topically to cynomolgus monkeys was associated with a lowering of intraocular pressure.

Each monkey was randomly assigned one experimental and one control eye. Slit lamp examination was done to ensure normal, healthy eyes prior to the experiment. The monkeys were anesthetized with 10 mg/kg ketamine hydrochloride administered intramuscularly. Supplemental anesthesia was administered as needed with additional 10 mg/kg/15 minutes. Baseline intraocular pressure (baseline A) was measured in each eye with a Digilab Pneumotonometer following topical anesthesia with one drop of 0.5% proparacaine hydrochloride. A solution of 75 mM N acetylcysteine (N-AC) was made in sterile water and the pH was adjusted to 7. One drop of 0.5% proparacaine HCl was given to each eye for anesthesia, followed by one drop of 75 mM N-AC to the experimental eye. No sham drop was given to the control eye. A total of 15 minutes elapsed from the time the drug was mixed to the time the drug was administered.

After a half hour, one drop of topical 0.5% proparacaine HCl was given to each eye prior to a second baseline pressure measurement (baseline B). A mixture of 130 mM ethacrynic acid (ECA) and 130 mM cysteine in 1/2000 benzalkonium were combined at the time the drugs were administered. One drop of 0.5% proparcaine HCl was given to each eye for anesthesia fol-

|  | | Mean Outflow Facilities μl/min/mmHg | | | Mean % Facility Change | | |
|---|---|---|---|---|---|---|---|
|  | N | Baseline | 5-hour | Difference | Experimental % | Control % | Difference % |
| 0.06 mM ECA alone | 12 E<br>C | 2.02<br>2.21 | 4.91<br>2.90 | 2.89<br>0.69 | 103 | 14 | 88 |
| 0.25/0.25 mM ECA/Cysteine | 10 E<br>C | 2.78<br>2.92 | 5.36<br>4.07 | 2.58<br>1.17 | 104 | 38 | 66 |
| 0.06/0.06 mM ECA/Cysteine | 4 E<br>C | 2.92<br>2.42 | 5.85<br>3.43 | 2.93<br>1.01 | 100 | 42 | 58 |
| 0.03/0.03 mM ECA/Cysteine | 6 E<br>C | 3.33<br>2.91 | 6.16<br>4.30 | 2.83<br>1.39 | 84 | 47 | 37 |
| 0.01/0.01 mM ECA/Cysteine | 10 E<br>C | 2.30<br>2.27 | 3.72<br>3.48 | 1.42<br>1.21 | 61 | 55 | 6 |
| 0.06/0.3 mM ECA/Cysteine | 10 E<br>C | 2.01<br>2.15 | 3.86<br>3.18 | 1.85<br>1.03 | 94 | 50 | 44 |
| 0.25/0.25 mM ECA/Cysteamine | 5 E<br>C | 2.35<br>2.38 | 4.22<br>3.06 | 1.87<br>0.68 | 70 | 10 | 60 |
| 0.25/0.25 mM ECA/Glutathione | 8 E<br>C | 2.29<br>2.32 | 3.83<br>1.64 | 1.54<br>0.68 | 72 | 30 | 42 |
| 0.25.0.25 mM ECA/Thiosalicylic Acid | 7 E<br>C | 2.46<br>2.22 | 3.87<br>2.64 | 1.41<br>0.42 | 57 | 20 | 37 |
| 0.25/0.25 mM ECA/N-acetyl-cysteine | 6 E<br>C | 2.47<br>2.29 | 4.73<br>3.45 | 2.26<br>1.16 | 96 | 51 | 45 |
| 0.25/0.25 mM ECA/N-acetyl-cysteamine | 8 E<br>C | 2.05<br>2.03 | 3.22<br>2.76 | 1.17<br>0.73 | 55 | 35 | 19 |

The number of calf eyes in each experiment is listed under N. The mean outflow facilities are the average microliters of Dulbecco's PBS+glucose that entered the calf eyes per mmHg per minute. The chart contains only the baseline and 5 hour measurements. The mean percent facility change calculates the change in fluid flow from the baseline measurement to the end of the experiment; comparing these values would be the best way to evaluate the drug effect.

lowed by one drop of ECA/cysteine in the experimental eye and one drop of 1:2000 benzalkonium chloride to the control eye. After 2 minutes, a second drop of ECA/cysteine was given to the experimental eye and a second drop of 1:2000 benzalkonium chloride to the control eye.

The monkeys were carefully examined with a slit lamp at 24 and 48 hours and additional pressures were taken with topical 0.5% proparacaine HCl. Results are summarized in the following monkey topical summary chart. The average baseline pressure was 25 mm Hg in the experimental eye and 25.5 mm Hg in the control eye. At 24 hours post experiment, the average pressure was 17 mm Hg in the experimental eye and 20.5 mmHg in the control eye. Therefore, the average lowering of pressure in the experimental eye was 8 mmHg at 24 hours associated with minimal, if any, corneal toxicity.

| MONKEY TOPICAL SUMMARY |||||||
|---|---|---|---|---|---|---|
| Pretreat 75 mM N-acetylcysteine (pH 7, 1 drop) Wait 30 min. 130 mM ECA/130 mM cysteine in 1/2000 benzalkonium chloride (pH 7, 2 drops) |||||||
| | MKY 51 || MKY 51 || MKY 51 ||
| | C | E | C | E | E | C |
| baseline A | 31 | 30 | 27 | 27 | 22 | 23 |
| baseline B | 28 | 30 | 28 | 27 | 21 | 22 |
| 24 hour | 29 | 16 | 27 | 20 | 17 | 19 |
| 48 hour | | | | | 20 | 20 |
| | MKY 51 || MKY 51 || MKY 2467* ||
| | E | C | C | E | E | C |
| baseline A | 28 | 28 | 21 | 21 | 22 | 23 |
| baseline B | 29 | 34 | 19 | 17 | 23 | 20 |
| 24 hour | 20 | 28 | 5 | 18 | 11 | 21 |
| 48 hour | | | | | 6 | 21 |
| | AVG E | STD | AVG C | STD |||
| baseline A | 25.0 | 3.5 | 25.5 | 3.5 |||
| baseline B | 24.5 | 4.8 | 25.2 | 5.3 |||
| 24 hour | 17.0 | 1.5 | 21.5 | 8.2 |||
| 48 hour | 13.0 | 7.0 | 20.5 | 0.5 |||

SLIT LAMP EXAM @ 24 HOURS:
5/6 Monkeys normal
*1/6 Monkeys diffuse stromal edema Similar experiments were performed on rabbits, except that the quantity of drops varied. Rabbits were randomly assigned on experimental and one control eye and received a single drop of topical 0.5% proparacaine HCl in each eye prior to baseline pressure (baseline A) measurements. A solution of 100 mM N-acetylcysteine was made in sterile water and the pH was adjusted to 7. A total of 15 minutes elapsed from the time the drug was mixed to the time the drops were administered. Another drop of topical 0.5% proparacinate HCl was given to each eye, followed by 2 drops of 100 mM N-acetylcysteine, separated by 2 minutes, to the experimental eye; no sham drops were given.

After a half hour, one drop of 0.5% topical proparacaine HCl was given to each eye and a second baseline pressure (baseline B) was measured. A mixture of 130 mM ECA and 130 mM cysteine was made in 1:2000 benzalkonium chloride and the pH was adjusted to pH 7. A total of 15 minutes elapsed between the time the drugs were combined to the time they were administered. A total of 8 drops of the ECA/cysteine mixture were given to the experimental eye, each drop separated by 2 minutes. At the same time, a total of 8 drops of 1:2000 benzalkonium chloride was given to the control eye, each drop separated by 2 minutes. The eyes were examined for corneal edema 24 hours and pressures were taken with 0.5% topical proparacaine HCl for anesthesia. The results are summarized in the following chart. ,220

| RABBIT TOPICAL EXPERIMENT ||||||
|---|---|---|---|---|---|
| Pretreat (2 drops) 100 mM N-acetylcysteine Topical (8 drops) 130 mM ECA/130 mM Cysteine (pH 7; pH 7) ||||||
| | #1 || #2 || #3 ||
| | E | C | E | C | C | E |
| baseline A | 22 | 22 | 24 | 23 | 20 | 23 |
| baseline B | 19 | 15 | 23 | 24 | 23 | 23 |
| 24 hr | 8 | 19 | 11 | 22 | 22 | 23 |
| | #4 || #5 || #6 ||
| | C | E | E | C | E | C |
| baseline A | 24 | 25 | 20 | 20 | 24 | 23 |
| baseline B | 23 | 24 | 22 | 21 | 23 | 23 |
| 24 hr | 19 | 23 | 19 | 20 | 25 | 24 |
| | #7 || #8 || #9 ||
| | E | C | E | C | E | C |
| baseline A | 26 | 26 | 30 | 26 | 25 | 29 |
| baseline B | 26 | 27 | 26 | 27 | 34 | 29 |
| 24 hr | 15 | 24 | 22 | 26 | 17 | 25 |
| | #10 || #11 || #12 ||
| | C | E | C | E | C | E |
| baseline A | 35 | 35 | 30 | 31 | 29 | 29 |
| baseline B | 37 | 37 | 34 | 30 | 34 | 37 |
| 24 hr | 14 | 20 | 24 | 19 | 12 | 10 |
| | AVG E | STD | AVG C | STD |||
| baseline A | 26.2 | 4.1 | 25.6 | 4.3 |||
| baseline B | 27.0 | 5.8 | 26.4 | 6.0 |||
| 24 hr | 17.7 | 5.3 | 20.9 | 4.2 |||

NOTE:
6/12 rabbits normal
4/12 rabbits trace edema
1/12 rabbits very red conjunctiva
1/12 rabbits 2+ cornea edema An additional rabbit experiment was performed identical to the preceding one except that 4 drops of pretreatment with 100 mM N-acetylcysteine were given prior to 8 drops of the 130 mM ECA and 130 mM cysteine mixture. Results were as follows:

| RABBIT TOPICAL EXPERIMENT ||||||
|---|---|---|---|---|---|
| Pretreat (4 drops) 100 mM NAC Topical (8 drops) 130 mM ECA/130 mM Cysteine (pH 7; pH 7) ||||||
| | #1 || #2 || #3 ||
| | E | C | E | C | C | E |
| baseline A | 22 | 21 | 21 | 19 | 23 | 23 |
| baseline B | 17 | 20 | 20 | 20 | 23 | 25 |
| 24 hr | 20 | 21 | 22 | 21 | 22 | 23 |
| | #4 || #5 || #6 ||
| | C | E | E | C | E | C |
| baseline A | 21 | 21 | 22 | 22 | 22 | 20 |
| baseline B | 22 | 22 | 24 | 24 | 23 | 22 |
| 24 hr | 26 | 25 | 24 | 24 | 22 | 26 |
| | #7 || #8 || #9 ||
| | C | E | C | E | C | E |
| baseline A | 24 | 28 | 27 | 28 | 29 | 31 |
| baseline B | 26 | 29 | 28 | 30 | 30 | 28 |
| 24 hr | 18 | 24 | 15 | 9 | 23 | 14 |
| | #10 || #11 || #12 ||
| | C | E | C | E | C | E |
| baseline A | 31 | 32 | 22 | 24 | 26 | 28 |
| baseline B | 35 | 35 | 36 | 32 | 33 | 33 |
| 24 hr | 18 | 16 | 22 | 21 | 24 | 13 |
| | AVG E | STD | AVG C | STD |||
| baseline A | 25.2 | 3.8 | 23.8 | 3.6 |||
| baseline B | 26.5 | 5.3 | 26.6 | 5.5 |||

| RABBIT TOPICAL EXPERIMENT | | | | |
|---|---|---|---|---|
| Pretreat (4 drops) 100 mM NAC | | | | |
| Topical (8 drops) 130 mM ECA/130 mM Cysteine (pH 7; pH 7) | | | | |
| 24 hr | 19.4 | 4.9 | 21.7 | 3.2 |

NOTE:
8/12 rabbits normal
2/12 rabbits trace corneal edema, red conjunctiva
1/12 rabbits 1+ corneal edema, red conjunctiva
1/12 rabbits 2+ corneal edema An additional rabbit experiment was performed, similar to the other experiments but without any pretreatment step. Rabbits were randomly assigned one experimental and one control eye and received a single drop of topical 0.5% proparacaine HCl in each eye prior to baseline pressure (baseline A) measurements. Some of the rabbits received a second baseline pressure measurement, a half hour later; these rabbits can be identified by a baseline B entry. The remaining rabbits only had one baseline pressure prior to the experiment Immediately following the last baseline pressures (A or B, depending upon the experiment), a mixture of 130 mM ECA and 130 mM cysteine was made in 1:20000 benzalkonium chloride and the pH was adjusted to pH 7. A total of 15 minutes elapsed between the time the drugs were combined to the time they were administered. A total of 8 drops of the ECA/Cysteine mixture were given to the experimental eye, each drop separated by 2 minutes. The eyes were examined for corneal toxicity at 24 hours and pressures were taken with 0.5% topical proparcaine HCl for anesthesia. Results from the experiment, including observations of corneal edema, are enclosed.

RABBIT TOPICAL EXPERIMENT
No Pre-Treatment
Topical (8 drops) 130 mM ECA/Cysteine (pH 7)

| | #1 | | #2 | | #3 | |
|---|---|---|---|---|---|---|
| | C | E | E | C | E | C |
| baseline A | | | 22 | 22 | 23 | 23 |
| baseline B | 22 | 24 | 20 | 20 | 23 | 24 |
| 24 hours | 23 | 19 | 16 | 20 | 10 | 21 |

| | #4 | | #5 | | #6 | |
|---|---|---|---|---|---|---|
| | C | E | C | E | E | C |
| baseline A | 21 | 21 | 24 | 23 | 21 | 21 |
| baseline B | 25 | 25 | 23 | 23 | 25 | 25 |
| 24 hr | 24 | 23 | 19 | 20 | 26 | 25 |

| | #6 | | #7 | | #8 | |
|---|---|---|---|---|---|---|
| | E | C | E | C | E | C |
| baseline A | 22 | 22 | 29 | 28 | 28 | 28 |
| baseline B | 22 | 21 | 30 | 29 | 25 | 25 |
| 24 hr | 22 | 24 | 19 | 29 | 11 | 24 |

| | #9 | | #10 | | #11 | |
|---|---|---|---|---|---|---|
| | E | C | C | E | C | E |
| baseline A | 21 | 23 | 35 | 34 | 27 | 25 |
| baseline B | 21 | 21 | 25 | 24 | 23 | 22 |
| 24 hr | 13 | 20 | 24 | 17 | 22 | 21 |

| | #12 | | #13 | | #14 | |
|---|---|---|---|---|---|---|
| | C | E | E | C | E | C |
| baseline A | 26 | 30 | 22 | 21 | 22 | 22 |
| baseline B | 23 | 20 | 26 | 24 | 25 | 21 |
| 24 hr | 20 | 14 | 23 | 30 | 19 | 18 |
| 48 hr | | | 23 | 30 | 19 | 18 |

| | #15 | | #16 | | #17 | |
|---|---|---|---|---|---|---|
| | E | C | C | E | C | E |
| baseline A | 21 | 18 | 27 | 30 | 31 | 33 |
| baseline B | 20 | 20 | | | | |
| 24 hr | 16 | 19 | 33 | 15 | 32 | 29 |
| 48 hr | 23 | 23 | 25 | 24 | 29 | 25 |

| | #18 | | #19 | | #20 | |
|---|---|---|---|---|---|---|
| | C | E | C | E | C | E |
| baseline A | 30 | 30 | 28 | 35 | 30 | 30 |
| baseline B | | | | | | |
| 24 hr | 30 | 28 | 34 | 27 | 30 | 20 |
| 48 hr | 26 | 27 | 26 | 28 | 25 | 26 |

| | #21 | | #22 | | #23 | |
|---|---|---|---|---|---|---|
| | C | E | C | E | C | E |
| baseline A | 29 | 26 | 30 | 30 | 34 | 36 |
| baseline B | | | | | | |
| 24 hr | 23 | 23 | 25 | 15 | 28 | 15 |
| 48 hr | 21 | 19 | 32 | 28 | 30 | 30 |

| | #24 | | #25 | | #26 | |
|---|---|---|---|---|---|---|
| | C | E | C | E | C | E |
| baseline A | 35 | 33 | 32 | 29 | 34 | 33 |
| baseline B | | | | | | |
| 24 hr | 33 | 15 | 30 | 15 | 31 | 15 |
| 48 hr | 30 | 30 | 27 | 14 | 29 | 25 |

| | #27 | | #28 | | #29 | |
|---|---|---|---|---|---|---|
| | C | E | C | E | C | E |
| baseline A | 38 | 35 | 31 | 32 | 29 | 29 |
| baseline B | | | 35 | 35 | 28 | 27 |
| 24 hr | 20 | 15 | 18 | 16 | 21 | 23 |
| 48 hr | 29 | 32 | | | | |

| | #30 | | #31 | | #32 | |
|---|---|---|---|---|---|---|
| | C | E | E | C | E | C |
| baseline A | 31 | 33 | 26 | 25 | 26 | 26 |
| baseline B | 29 | 30 | | | | |
| 24 hr | 26 | 11 | 18 | 23 | 21 | 20 |

| | #33 | | #34 | | #35 | |
|---|---|---|---|---|---|---|
| | E | C | E | C | E | C |
| baseline A | 28 | 26 | 21 | 23 | 24 | 23 |
| baseline B | | | | | | |
| 24 hr | 24 | 23 | 18 | 22 | 17 | 22 |

| | #36 | |
|---|---|---|
| | E | C |
| baseline A | 26 | 27 |
| baseline B | | |
| 24 hr | 11 | 25 |

| | AVG E | STD | AVG C | STD |
|---|---|---|---|---|
| baseline A | 27.4 | 4.7 | 27.2 | 4.7 |
| baseline B | 24.5 | 3.8 | 24.3 | 3.7 |
| 24 hr | 18.0 | 5.0 | 24.8 | 4.4 |
| 48 hr | 24.8 | 4.6 | 27.0 | 3.5 |

NOTES:
16/37 NORMAL
6/37 TRACE EDEMA
4/37 MILD EDEMA
2/37 DIFFUSE EDEMA
6/37 2+ EDEMA
4/37 RED CONJUNCTIVA
1/37 CHEMOSIS

Those skilled in the art will be able to recognize or ascertain with no more than routine experimentation numerous equivalents to the specific products an processes described herein.

Such equivalents are considered to be within the scope of the invention and are intended to be covered by the following claims in which I claim:

1. In a method for treating or preventing glaucoma wherein a molecule having one or more groups capable of reacting with sulfhydryl groups in the trabecular meshwork of the eye is delivered to the trabecular meshwork in an amount sufficient to increase aqueous humor outflow, the improvement comprising,
administering a masking agent to the eye in conjunction with delivering the molecule in sufficient amount to prevent a medically unacceptable side effect which would otherwise occur without administration of the masking agent.

2. The improvement of claim 1 wherein the masking agent and molecule are administered separately.

3. The improvement of claim 1 wherein the masking agent and molecule are administered as an adduct.

4. The improvement of claim 1 wherein the masking agent is present in molar excess relative to the molecule.

5. The improvement of claim 1 wherein the molecule is present in molar excess relative to the masking agent.

6. The improvement of claims 1, 2, 3, 4 or 5 wherein the molecule is ethacrynic acid or an analog thereof.

7. The improvement of claims 1, 2, 3, 4 or 5 wherein the masking agent is selected from the group consisting of cysteine and N-acetylcysteine.

8. The improvement of claims 1, 2, 3, 4 or 5 wherein the molecule is ethacrynic acid and the masking agent is selected from the group consisting of cysteine and N-acetylcysteine.

9. The improvement of claims 1, 3 or 4 further comprising administering a delivery enhancing agent to the eye.

10. The improvement of claim 6 further comprising administering a delivery enhancing agent to the eye.

11. The improvement of claim 7 further comprising administering a delivery enhancing agent to the eye.

12. The improvement of claim 8 further comprising administering a delivery enhancing agent to the eye.

13. The improvement of claims 1, 2, 3, 4 or 5 wherein the masking agent is topically administered to the eye in conjunction with delivering the molecule.

14. The improvement of claims 1, 2, 3, 4 or 5 wherein the molecule is ethacrynic acid.

15. A method of treating or preventing glaucoma comprising administrating topically to the eye a therapeutically effective amount of an adduct of a masking agent and a molecule capable of reacting with sulfhydryl groups in the trabecular meshwork and capable of increasing aqueous outflow.

16. A method as claimed in claim 14 wherein the molecule is ethacrynic acid or an analog thereof.

17. A method as claimed in claim 14 wherein the masking agent is selected from the group consisting of cysteine and N-acetycysteine.

18. A method as claimed in claim 15 wherein the masking agent is selected from the group consisting of cysteine and N-acetycysteine.

19. A method as claimed in claim 17 wherein the molecule is ethacrynic acid.

20. A method as claimed in claims 14, 15, 16, 17 or 18 further comprising administering masking agent to the eye prior to administering the adduct.

21. A pharmaceutically acceptable ophthalmic preparation comprising
an adduct of a molecule having one or more groups capable of reacting with sulfhydryl groups in the trabecular meshwork of the eye to increase aqueous humor outflow, and
a delivery enhancing agent.

22. An ophthalmic preparation as claimed in claim 21 wherein the adduct is an adduct of ethacrynic acid or an analog thereof.

23. An ophthalmic preparation as claimed in claim 21 wherein the adduct is an ethacrynic acid adduct.

24. A pharmaceutically acceptable opthalmic preparation comprising an adduct of a molecule having one or more groups capable of reacting with sulfhydryl in a trabecular meshwork of the eye to increase aqueous humor outflow and a masking agent, wherein the masking agent is present in molar excess in relation to the molecule.

25. An ophthalmic preparation as claimed in claim 24 wherein the adduct is an adduct of ethacrynic acid or an analog thereof.

26. An ophthalmic preparation as claimed in claim 24, wherein the adduct is an ethacrynic acid adduct.

27. The method of claim 14 wherein the molecule is ethacrynic acid.

* * * * *

UNITED STATES PATENT AND TRADEMARK OFFICE
CERTIFICATE OF CORRECTION

PATENT NO. : 5,306,731
DATED : April 26, 1994
INVENTOR(S) : David L. Epstein It is certified that error appears in the above-identified patent and that said Letters Patent is hereby corrected as shown below:

Col. 2, line 48-delete"sulfhydryl reactive" and replace with "sulfhydryl-reactive"

Col. 5, line 9 - delete "produce II" and replace with "product II"

Col. 13, line 34 - delete "on" and replace with "one"

Ccl. 13, line 60 - delete "220"

Col. 17, line 39 - delete "of" and replace with "for"

Signed and Sealed this

Twenty-third Day of August, 1994

*Attest:*

BRUCE LEHMAN

*Attesting Officer*     *Commissioner of Patents and Trademarks*